United States Patent
Fukui et al.

(10) Patent No.: US 8,148,090 B2
(45) Date of Patent: Apr. 3, 2012

(54) METHOD FOR PREDICTION OF POSTOPERATIVE PROGNOSIS AND DIAGNOSIS KIT

(75) Inventors: Yousuke Fukui, Tokushima (JP); Atsushi Ogiwara, Tokyo (JP); Shingo Akimoto, Kanagawa (JP); Takao Kawakami, Saitama (JP); Takashi Hirano, Tokyo (JP); Junichi Maeda, Tokyo (JP); Harubumi Kato, Tokyo (JP)

(73) Assignee: Medical Proteoscope Co., Ltd., Tokyo (JP)

( * ) Notice: Subject to any disclaimer, the term of this patent is extended or adjusted under 35 U.S.C. 154(b) by 0 days.

(21) Appl. No.: 12/738,522

(22) PCT Filed: Oct. 17, 2008

(86) PCT No.: PCT/JP2008/069289
§ 371 (c)(1),
(2), (4) Date: Apr. 16, 2010

(87) PCT Pub. No.: WO2009/051277
PCT Pub. Date: Apr. 23, 2009

(65) Prior Publication Data
US 2010/0221744 A1    Sep. 2, 2010

(30) Foreign Application Priority Data
Oct. 18, 2007  (JP) ................................. 2007-271139

(51) Int. Cl.
*G01N 33/53* (2006.01)
(52) U.S. Cl. .......................................... 435/7.1; 436/518
(58) Field of Classification Search .................. None
See application file for complete search history.

(56) References Cited

U.S. PATENT DOCUMENTS

| | | | |
|---|---|---|---|
| 5,716,787 A * | 2/1998 | Dunn et al. ..................... 435/7.1 |
| 7,550,256 B2 * | 6/2009 | Georges et al. ................... 435/4 |
| 2004/0004239 A1* | 1/2004 | Madurawe .................... 257/298 |
| 2006/0275810 A1* | 12/2006 | Georges et al. ................... 435/6 |

FOREIGN PATENT DOCUMENTS

| | | |
|---|---|---|
| JP | 2007-6791 A | 1/2007 |
| JP | 2007-135466 A | 6/2007 |
| WO | 2007/043418 A1 | 4/2007 |
| WO | WO 2007/043418 A1 | 4/2007 |

OTHER PUBLICATIONS

Chen et al., "Discordant Protein and mRNA Expression in Lung Adenocarcinomas", Molecular & Cellular Proteomics, 2002, vol. 4, pp. 304-313.
Larsen et al., "Gene Expression Signature Predicts Recurrence in Lung Adenocarcinoma", Clin Cancer Res, May 15, 2007, vol. 13, No. 10, pp. 2946-2954.
Database WPI Week 200742, Thomson Scientific, London, GB; AN 2007-437387; XP 002598064 (JP 2007-135466 A).
Database WPI Week 200746, Thomson Scientific, London, GB; AN 2007-476658; XP002598063 (WO 2007/043418 A1).
Jana et al., "A Specific Isoform of Nonmuscle Myosin II-C is Required for Cytokinesis in a Tumor Cell Line," The Journal of Biological Chemistry, (Aug. 25, 2006) vol. 281, No. 34, pp. 24662-24670.
Kato et al., "The Role of Actin-Binding Protein Filamin A in Cellular Stiffness and Morphology Studied by Wide-Range Scanning Probe Microscopy," Japanese Journal of Applied Physics (2006), vol. 45, No. 3B, pp. 2328-2332.
Maeda et al., "Proteomic analysis of stage I primary lung adenocarcinoma aimed at individualisation of postoperative therapy," British Journal of Cancer (2008), vol. 98, pp. 596-603.
Nakano et al., "Evaluations of biomarkers associated with 5-FU sensitivity for non-small-cell lung cancer patients postoperatively treated with UFT," British Journal of Cancer (2006), vol. 95, pp. 607-615.
Rivero et al., "Analysis of myosin heavy chains at the protein level in horse skeletal muscle," Journal of Muscle Research and Cell Motility (1999), vol. 20, pp. 211-221.
Supplementary European Search Report dated Sep. 17, 2010, issued in corresponding European Patent Application No. 08839646.0.

* cited by examiner

*Primary Examiner* — Jacob Cheu
(74) *Attorney, Agent, or Firm* — Birch, Stewart, Kolasch & Birch, LLP (57) ABSTRACT

The present invention relates to a method for predicting the postoperative prognosis of a lung adenocarcinoma patient with high sensitivity and/or specificity by identifying a protein with an expression level that specifically varies in a lung adenocarcinoma patient, comprising: step (a) of determining expression levels of myosin IIA and/or vimentin in a biological sample collected from a lung adenocarcinoma patient; and step (b) of predicting or determining a prognosis based on the expression levels of myosin IIA and/or vimentin obtained as a result of determination.

6 Claims, 4 Drawing Sheets

METHOD FOR PREDICTION OF POSTOPERATIVE PROGNOSIS AND DIAGNOSIS KIT

TECHNICAL FIELD

The present invention relates to a method for predicting the postoperative prognosis of a lung adenocarcinoma patient and a diagnosis kit for determining such prognosis.

BACKGROUND ART

Today, lung cancer is the primary cause of death from cancer in almost all developed countries, including Japan, although a variety of therapeutic methods have been improved. Further, in spite of increased opportunities for early detection of lung cancer, approximately 60,000 lung cancer patients die in Japan every year. The main cause of death of lung cancer patients treated with surgical therapy is distant metastasis. Distant metastasis, including intrapulmonary metastasis observed in non-small-cell lung cancer patients, is often observed among patients treated by surgical resection alone. This is because, in such patients' cases, micrometastatic foci are already present at the time of surgical resection. The prognosis of a non-small-cell lung cancer patient can be improved in some cases involving the use of postoperative adjuvant chemotherapy, which is performed to suppress micrometastasis recurrence. However, the effects of postoperative adjuvant chemotherapy for non-small-cell lung cancer patients treated with a radical surgery have been often controversial since the 1980s. Even in 2003, the effects of postoperative adjuvant chemotherapy were still not verified in terms of efficacy (Scagliotti G V, Frossati R, Torri V, Crino L, Giaccone G, Silvano G, Martelli M, Clerici M, Cognetti F, and Tonato M., J Nat Cancer Inst. (2003) 95: 1453-1461). In 2004, some reports on the effects of postoperative adjuvant chemotherapy were published and data showing the efficacy of the therapy were disclosed (Winton T, Livingston R, Johnson D, Rigas J, Johnston M, and Butts C, Cormier Y (2005) N Engl J Med 352: 2589-2597; Strauss G M, Herndon J, Maddaus M A, Johnstone D W, Johnson E A, Watson D M, Sugarbaker D J, Schilsky R L, and Green M R. (2004) Proc Am Soc Clin Oncol 23: 621; Arriagada R, Bergman B, Dunant A, Le Chevalier T, Pignon J P, and Vansteenkiste J. (2004) N Engl J Med 350: 351-360).

Also, in 2004, it was reported that primary lung adenocarcinoma patients in stage I were confirmed to have improved prognoses as a result of postoperative adjuvant chemotherapy with oral tegafur-uracil (a mixed formulation with a molar ratio of 4:1; hereinafter referred to as "UFT") compared with patients treated by surgery alone (Kato H, Ichinose Y, Ohta M, Hata E, Tsubota N, Tada H, Watanabe Y, Wada H, Tsuboi M, Hamajima N, and Ohta M. (2004) N Engl J Med 350: 1713-1721). However, only 15% of primary lung adenocarcinoma patients in stage IB can be expected to have improved prognoses as a result of postoperative adjuvant chemotherapy with oral tegafur-uracil. Therefore, if biomarkers that allow reasonable and objective prediction/determination of the prognosis of a patient treated with postoperative chemotherapy can be discovered in view of molecular biology, such biomarkers would be significantly useful.

Hitherto, as a method for identifying markers associated with drug efficacy, an immunobiochemical identification method has been known. In recent years, as a part of the post-genome study, an approach called pathological proteomics has been gaining attention. Specifically, it is a method comprising simultaneously analyzing actually expressed proteins in a blanket manner and searching for marker proteins for diseases. Examples of such pathological proteomics approach include a method using matrix assisted laser desorption/ionization (MALDI) time-of-flight (TOF) mass spectrometry (MS) and a method using liquid chromatography ion trap mass mass spectrometer.

However, sufficient analysis performance cannot be realized by the above conventional pathological proteomics approach in the analysis of clinical pathology, by comparing protein expression patterns of biological samples from healthy individuals and those from patients, especially in a case where large variances in many factors are expected, and furthermore, a level of difference of each factor is too slight to distinguish it from an individual difference or a measurement error.

Therefore, in Patent Document 1, the present inventors reported a sample analysis method and a sample analysis program with excellent analysis performance, which allow pathological proteomics analysis. In addition, they reported "a lung adenocarcinoma lymph node metastasis diagnosis method and a diagnosis kit," which have been completed with the use of the above method and program (Patent Document 2).

Non-muscle-type myosin IIA is a main constituent of the actomyosin cytoskeleton and known to be generally involved in the posterior-side contraction of cells during cell migration. Cellular projections were thought to be controlled via actin filament polymerization in a myosin IIA-independent manner. In recent years, it has been reported that myosin IIA is involved in formation of cellular projections associated with cell migration of non-cancer cells. However, the way in which myosin IIA functions during cell migration is unknown. Obviously, myosin IIA is involved in cell migration. However, in the past studies, protein profiles at expression levels observed during cell migration of cancer cells and isotypes of plural forms of myosin IIA were merely evaluated.

In recent years, clinical studies of non-small-cell lung cancer have showed that there is a correlation between the expression levels of myosin light chain kinase that causes myosin II activation and metastasis/recurrence, and that myosin IIA activation is a metastatic factor (Non-Patent Document 1). The important role of myosin IIA in metastatic cancer cells was suggested by an indirect study focusing on the small calcium-binding protein metastin 1. In many metastatic culture cell lines, the expression of metastin 1 is intensified and the metastatic nature is enhanced as a result of introduction of metastin 1 into culture cells (Non-Patent Document 2). Further, the main target molecule of metastin 1 is thought to be myosin IIA (Non-Patent Document 3). In addition, it has been shown that metastin 1 and myosin IIA coexist at an identical location in a tip portion of a migrating cancer cell (Non-Patent Document 4), and therefore metastin 1 influences phosphorylation caused by protein kinase, which is thought to control polymerization of myosin IIA and filaments (Non-Patent Documents 5 and 6).

Vimentin, which has a molecular weight of 57 kDa, is an intermediate filament protein that is expressed in the early phase of cell differentiation so as to be widely distributed. For all initial cell types, the expression of vimentin is observed. However, in many non-mesenchymal cells, vimentin is replaced by a different intermediate filament protein over the course of differentiation. Vimentin is expressed in a variety of mesenchymal cells such as fibroblasts and endothelial cells. There are several cell types of vimentin, which are derived from mesoderm and granulosa cells in mesothelia and ovaries. During the course of differentiation, epithelial cells acquire mesenchymal phenotypes that are essential for organogenesis in a reversible or irreversible manner. Epithelial-interstitial transition (interaction) in morphogenesis causes abnormal expression in a variety of epithelial cancers, including thyroid gland cancer, liver cancer, kidney cancer, prostate cancer, mammary gland cancer, and lung cancer, during tumorigenesis (Non-Patent Documents 7 and 8). Regarding general characteristics observed over the course of tumorigenesis, acquisition of interstitial phenotypes associated with loss of normal epithelial phenotypes, loss of polarizing epithelial morphology, and gradual acquisition of phenotypes (i.e., partial or entire motility and invasiveness) can be mentioned (Non-Patent Document 9).

Further, the collapse of epithelial morphology involves abnormal control of adhesion molecules, abnormal expression of N-cadherin, and epithelial-interstitial interaction (transition) with the expression of molecules such as fibronectin and vimentin in epithelial cells, such molecules originally being expressed in the interstitium. There is a correlation between abnormal expression of vimentin in tumors or transformants and increased motility, invasiveness, and poor prognosis (Non-Patent Documents 10 and 11). In lungs, vimentin is present in fibroblasts, smooth muscles, endothelia, and lymphoid lineage cells; however, it is not expressed in normal bronchial epithelial cells. A study conducted in recent years reported that vimentin-positive tumor cells in a fibrotic portion are mainly involved in tumor fibrosis accompanied by epithelial-interstitial transition (interaction), corresponding to the other study results (Non-Patent Document 12). In fact, acquisition of mesenchymal phenotypes relates to the expression of a protein serving as a mesenchymal marker and abnormal extracellular matrix deposition. Similar findings have been reported with the use of other models of, for example, progressive renal fibrosis in which the existence of vimentin-positive epithelial cells is associated with the degree of increase in fibrotic tissue (Non-Patent Documents 13 and 14).

Regarding the role of a marker, myosin has been known as a marker for differential diagnosis of rhabdomyosarcoma, and vimentin has been known as a marker protein for a variety of benign and malignant tumors such as malignant melanoma (Patent Document 3). Particularly recently, they have been studied as immunohistochemical markers for distinguishing epithelial malignant mesothelioma and lung adenocarcinoma (Non-Patent Documents 15 and 16).

Patent Document 1: WO 2004/090526
Patent Document 2: JP Patent No. 2006-53113
Patent Document 3: JP Patent No. 2006-518982
Non-Patent Document 1: Tumour Biol 26 153-157, 2005
Non-Patent Document 2: Oncogene 8 999-1008, 1993
Non-Patent Document 3: J Biol Chem 281 677-680, 2006
Non-Patent Document 4: J Biol Chem 278 30063-30073, 2003
Non-Patent Document 5: Biochemistry 44 6867-6876, 2005
Non-Patent Document 6: Biochemistry 42 14258-14266, 2003
Non-Patent Document 7: Nat Rev Cancer 2 442-454, 2002
Non-Patent Document 8: Cell 105 425-431, 2001
Non-Patent Document 9: J Cell Biol 135 1643-1654, 1996
Non-Patent Document 10: J Pathol 180 175-180, 1996
Non-Patent Document 11: Am J Pathol 150 483-495, 1997
Non-Patent Document 12: Lab Invest 84 999-1012, 2004
Non-Patent Document 13: Virchows 433 359-367, 1998
Non-Patent Document 14: Kidney Int 58 587-597, 2000
Non-Patent Document 15: The American Journal of Surgical Pathology 27(8) 1031-1051, 2003
Non-Patent Document 16: Pathology International 57 190-199, 2007

DISCLOSURE OF THE INVENTION

At present, there have been no findings regarding proteins with the expression levels varying specifically in lung adenocarcinoma patients. As a matter of course, the correlation between the expression profiles of myosin IIA or vimentin and the prognoses of lung adenocarcinoma patients has remained unknown. Therefore, the object determined by the present inventors is to provide a method and test kit for predicting the postoperative prognosis of a lung adenocarcinoma patient with high sensitivity and/or specificity by identifying a protein with an expression level that specifically varies in a lung adenocarcinoma patient with the use of the analysis method or analysis program disclosed in Patent Document 1.

In order to achieve the above object, the present inventors have identified markers that are associated with a postoperative prognosis of lung adenocarcinoma and with the effects obtained by applying the sample analysis method or the sample analysis program that have been preliminarily disclosed (Patent Document 1) whereby pathological proteomics analysis can be carried out and excellent analysis performance can be realized. This has led to the completion of the present invention.

Specifically, the present invention encompasses the following.

(1) A method for predicting a postoperative prognosis, comprising:
  step (a) of determining expression levels of myosin IIA and/or vimentin in a biological sample collected from a lung adenocarcinoma patient; and
  step (b) of predicting or determining a prognosis based on the expression levels of myosin IIA and/or vimentin obtained as a result of determination.

(2) The method for predicting a prognosis according to (1), wherein the expression level of at least one peptide selected from the group of peptides having the amino acid sequences listed in the PEPTIDE_SEQ column of Table 1 is determined in step (a).

TABLE 1

| Protein Name | Name | Peptide | Fraction | PEPTIDE_SEQ |
|---|---|---|---|---|
| Myosin IIA | MYH9 | MYH9_1 | Insoluble | IRELESQISELQEDLESER |
| | | MYH9_2 | Insoluble | KANLQIDQINTDLNLER |
| | | MYH3_3 | Insoluble | HEMPPHIYAITDTAYR |
| Vimentin | VIM | VIM_1 | Insoluble | ETNLDSLPLVDTHSK |
| | | VIM_2 | Insoluble | NLQEAEEWYK |
| | | VIM_3 | Insoluble | LGDLYEEEMR |
| | | VIM_4 | Insoluble | LLQDSVDFSLADAINTEFK |

(3) The method for predicting a prognosis according to (1), wherein the expression levels of myosin IIA and/or vimentin are determined by immunohistochemical staining with the use of a monoclonal antibody in step (a).

(4) The method for predicting a prognosis according to (1), wherein the expression levels of myosin IIA and/or vimentin are determined by allowing an extract obtained from the biological sample collected from the lung adenocarcinoma patient to come into contact with a support on which a monoclonal antibody has been immobilized in step (a).

(5) The method for predicting a prognosis according to any one of (1) to (4), wherein the lung adenocarcinoma patient is an early lung adenocarcinoma patient diagnosed as stage I by pathological tissue diagnosis.

(6) A test kit for predicting the prognosis of a lung adenocarcinoma patient, which comprises at least one antibody that specifically binds to myosin IIA and/or antibody that specifically binds to vimentin.

(7) The test kit according to (6), wherein the antibody is an antibody that specifically binds to a peptide selected from the group of peptides having the amino acid sequences listed in the PEPTIDE_SEQ column of Table 1.

(8) The test kit according to (6), wherein the antibody is a monoclonal antibody.

(9) The test kit according to (6), wherein the antibody is immobilized on a support.

This description includes part or all of the contents as disclosed in the description and/or drawings of Japanese Patent Application No. 2007-271139, which is a priority document of the present application.

BRIEF DESCRIPTION OF THE DRAWINGS

FIG. 1A shows a comparison of signal intensities in groups of peptides from an identical protein detected by liquid chromatography-mass spectrometry (LC-MS). Comparison was carried out for each group (U0R0, U0R1, U1R0, and U1R1). The vertical axis represents values normalized based on signal intensities determined by LC-MS. For each boxplot (box-and-whisker diagram or plot), the upper edge and the lower edge of a box indicate the upper quartile point and the lower quartile point, respectively. The upper and lower horizontal lines drawn outside of the box indicate the upper adjacent value and the lower adjacent value, respectively. Herein, the upper adjacent value corresponds to the maximum value not more than Q3+1.5×(Q3−Q1) or less. The lower adjacent value corresponds to the minimum value not less than Q1−1.5×(Q3−Q1) or more. Each black triangle represents a median value and each black rectangle represents an outlier. FIG. 1A shows distribution of myosin IIA-derived signal intensities for groups of the following cases: U0R0: cases with nonmetastatic recurrence after the non-implementation of postoperative adjuvant chemotherapy; U0R1: cases with metastatic recurrence after the non-implementation of postoperative adjuvant chemotherapy; U1R0: cases with nonmetastatic recurrence after the implementation of postoperative adjuvant chemotherapy; and U1R1: cases with metastatic recurrence after the implementation of postoperative adjuvant chemotherapy.

FIG. 1B shows a comparison of signal intensities in groups of peptides from an identical protein detected by liquid chromatography-mass spectrometry (LC-MS). Comparison was carried out for each group (U0R0, U0R1, U1R0, and U1R1). The vertical axis represents values normalized based on signal intensities determined by LC-MS. For each boxplot (box-and-whisker diagram or plot), the upper edge and the lower edge of a box indicate the upper quartile point and the lower quartile point, respectively. The upper and lower horizontal lines drawn outside of the box indicate the upper adjacent value and the lower adjacent value, respectively. Herein, the upper adjacent value corresponds to the maximum value not more than Q1+1.5×(Q3−Q1) or less. The lower adjacent value corresponds to the minimum value not less than Q3−1.5×(Q3−Q1) or more. Each black triangle represents a median value and each black rectangle represents an outlier. FIG. 1B shows distribution of vimentin-derived signal intensities for groups of the following cases: U0R0: cases with nonmetastatic recurrence after the non-implementation of postoperative adjuvant chemotherapy; U0R1: cases with metastatic recurrence after the non-implementation of postoperative adjuvant chemotherapy; U1R0: cases with non-metastatic recurrence after the implementation of postoperative adjuvant chemotherapy; and U1R1: cases with metastatic recurrence after the implementation of postoperative adjuvant chemotherapy.

BEST MODE FOR CARRYING OUT THE INVENTION

Hereinafter, a method and/or a test kit for predicting the postoperative prognosis of a lung adenocarcinoma patient of the present invention are described below in detail.

The method for predicting/determining the postoperative prognosis of a lung adenocarcinoma patient comprises: step (a) of determining the expression levels of myosin IIA and/or vimentin in a biological sample such as tissue, blood, or urine collected from a patient; and step (b) of predicting or determining the prognosis based on the expression levels of myosin IIA and/or vimentin obtained as a result of determination. In addition, in step (a), the expression level of either myosin IIA or vimentin may be determined. However, the expression levels of both substances are preferably determined. Also in step (b), preferably, the prognosis is predicted or determined based on the expression levels of myosin IIA and vimentin determined in step (a). However, it is also possible to predict or determine the prognosis based on the expression level of either myosin IIA or vimentin determined in step (a).

Further, determination of the expression levels of myosin IIA and vimentin is not particularly limited. However, the expression level of, for example, at least one peptide selected from the group of peptides having the amino acid sequences listed in the PEPTIDE_SEQ column of Table 2 can be determined.

TABLE 2

| Protein Name | Name | Peptide | Fraction | PEPTIDE_SEQ |
|---|---|---|---|---|
| Myosin IIA | MYH9 | MYH9_1 | Insoluble | IRELESQISELQEDLESER |
| | | MYH9_2 | Insoluble | KANLQIDQINTDLNLER |
| | | MYH3_3 | Insoluble | HEMPPHIYAITDTAYR |
| Vimentin | VIM | VIM_1 | Insoluble | ETNLDSLPLVDTHSK |
| | | VIM_2 | Insoluble | NLQEAEEWYK |
| | | VIM_3 | Insoluble | LGDLYEEEMR |
| | | VIM_4 | Insoluble | LLQDSVDFSLADAINTEFK |

In Table 2, the "Protein Name" column contains general protein names. In addition, the "Name" column contains "Symbol" names from "EnTrez Gene" database provided by NCBI. The "Peptide" column contains the codes of identified peptides. The "Fraction" column contains fractions fractionated after protein extraction. Further, the "PEPTIDE_SEQ" column contains peptide partial sequences identified based on MS/MS spectra. In addition, SEQ ID NO: 1 represents the amino acid sequence of a peptide designated as MYH9__1. SEQ ID NO: 2 represents the amino acid sequence of a peptide designated as MYH9__2. SEQ ID NO: 3 represents the amino acid sequence of a peptide designated as MYH9__3. SEQ ID NO: 4 represents the amino acid sequence of a peptide designated as VIM__1. SEQ ID NO: 5 represents the amino acid sequence of a peptide designated as VIM__2. SEQ ID NO: 6 represents the amino acid sequence of a peptide designated as VIM__3. SEQ ID NO: 7 represents the amino acid sequence of a peptide designated as VIM__4.

Proteins listed in Table 2 have been newly identified as being associated with prognoses by the analysis method for analyzing components contained in samples that was previously developed by the present inventors. Therefore, in the method for predicting a prognosis of the present invention, first, the expression levels of myosin IIA and/or vimentin in a biological sample such as tissue, blood, or urine collected from a lung adenocarcinoma patient are determined.

Herein, a lung adenocarcinoma patient is not particularly limited as long as the patient is a postoperative lung adenocarcinoma patient. Such patient may be a patient under examination for adjuvant chemotherapy, a patient undergoing adjuvant chemotherapy, or a patient for whom follow-up without adjuvant chemotherapy is planned. In particular, an early lung adenocarcinoma patient diagnosed as stage I by pathological tissue diagnosis is preferably selected as a lung adenocarcinoma patient. In addition, the method for predicting a prognosis of the present invention does not comprise directly applying treatment to a lung adenocarcinoma patient. The method is carried out using a biological sample such as tissue, blood, or urine collected from a patient.

A biological sample used in the method for predicting a prognosis of the present invention is not limited to the following examples. Specific examples of a biological sample that can be used include whole blood, plasma, serum, and cellular components such as hemocytes collected from a patient under examination for adjuvant chemotherapy, a patient undergoing adjuvant chemotherapy, and a patient for whom follow-up without adjuvant chemotherapy is planned. Also, tissue and urine samples collected from the above patients can be used.

Specifically, in order to determine the expression levels of myosin IIA and/or vimentin in a biological sample collected from a lung adenocarcinoma patient (hereinafter collectively referred to as "analyte protein" in some cases), for example, a monoclonal antibody against an analyte protein can be used.

In addition, the above antibody is not particularly limited as long as it binds to an analyte protein used as an antigen. Examples of such antibody that can be adequately used include a mouse antibody, a rat antibody, a rabbit antibody, and a sheep antibody. Such antibody may be a polyclonal antibody or a monoclonal antibody. However, a monoclonal antibody is preferably used since it can stably produce a uniform antibody. A polyclonal antibody and a monoclonal antibody can be produced by a method known to persons skilled in the art.

A hybridoma that produces a monoclonal antibody can be produced in a manner described below basically with the use of a known technique. Specifically, such a hybridoma can be produced by carrying out immunization with the use of a desired antigen or a cell capable of expressing a desired antigen as a sensitizing antigen by a general immunization method, fusing an obtained immunocyte with a known parent cell by a general cell fusion method, and screening for a monoclonal antibody producing cell (hybridoma) by a general screening method. A hybridoma can be produced according to, for example, the method of Milstein et al. (Kohler. G. and Milstein, C., Methods Enzymol. (1981) 73: 3-46).

Herein, in order to produce a monoclonal antibody, an analyte protein or a fragment of the protein (e.g., a peptide having the amino acid sequence listed in the PEPTIDE_SEQ column of Table 2) can be used as an antigen. In addition, a cell capable of expressing an analyte protein or a fragment of the protein can be used as an antigen. In addition, a cell capable of expressing an analyte protein or a fragment of the protein can be readily obtained by persons skilled in the art according to, for example, the method described in Molecular Cloning: A Laboratory Manual, $2^{nd}$ edition, vol. 1-3, Sambrook, J. et al, Cold Spring Harbor Laboratory Press, New York, 1989.

The amino acid sequence of an analyte protein or nucleotide sequence encoding the protein can be obtained based on the "Symbol" name (from "EnTrez Gene" database provided by NCBI) listed in the "Name" column in Table 2 and/or the amino acid partial sequence listed in the "PEPTIDE_SEQ" column. In addition, persons skilled in the art can readily obtain an analyte protein or a fragment of the protein based on the obtained amino acid sequence and the nucleotide sequence according to a general method.

The thus obtained monoclonal antibody can be used as a test reagent for quantification of an analyte protein, enzyme-linked immunosorbent assay (ELISA), enzyme immunodot assay, radioimmunoassay, agglutination assay, or a different well-known immunoassay method. In addition, the above monoclonal antibody is preferably labeled. For labeling, an enzyme, a fluorescent substance, a chemiluminescent substance, a radioactive material, a staining substance, or the like, which is known in the art, can be used as a labeling compound.

Meanwhile, the diagnosis test kit for predicting a prognosis of the present invention comprises an antibody that specifically binds to myosin IIA and/or an antibody that specifically binds to vimentin. The test kit used herein may comprise, for example, a plurality of antibodies that specifically bind to myosin IIA. Such a plurality of antibodies are preferably antibodies each having a different epitope portion. Similarly, the test kit may comprise a plurality of antibodies that specifically bind to vimentin. In addition, the antibody used herein is preferably a monoclonal antibody.

For instance, the test kit can be obtained by coating a support (e.g., the inner wall of a microtiter well) with the above monoclonal antibody (or a fragment thereof). Examples of such support include: a microtiter plate made of polystyrene, polycarbonate, polypropylene, or polyvinyl; a test tube; a capillary, beads; a membrane; and a filter.

In addition, the test kit comprises at least one antibody selected from the group consisting of antibodies. Preferably, it comprises two antibodies from myosin IIA and vimentin.

As described above, in the method for predicting a prognosis of the present invention, the expression level of an analyte protein in a biological sample such as tissue, blood, or urine collected from a lung adenocarcinoma patient is determined, followed by preliminary prediction of a postoperative prognosis or prediction of therapeutic effects for the lung adenocarcinoma patient based on the expression level. When the expression level of myosin IIA or vimentin is high, it can be determined that the postoperative prognosis of a lung adenocarcinoma patient is poor.

More specifically, a proportion (relative value) is obtained by dividing the expression level of an analyte protein by the expression level of a protein that is structurally expressed in a biological sample or by the amount of a different protein (e.g., serum albumin) that is determined by a general serological assay. When the value significantly exceeds the standard value, a patient can be diagnosed as having a poor prognosis. The standard value used herein can be designated as, for example, the mean value of the expression levels (relative values) of analyte proteins in the group of lung adenocarcinoma patients who have been found to experience recurrence within 5 years. In addition, the standard value can be determined as, for example, the mean value of the expression levels (relative values) of analyte proteins in a group of lung adenocarcinoma patients who have been found to experience no recurrence within 5 years (5-year survival). The standard value can be designated for each analyte protein.

The expression "significantly exceeds" used herein indicates a case in which the expression level exceeds the standard value with a statistically significant difference. Specifically, such expression indicates that "the proportion (relative value) calculated based on the protein expression level determined in step (a)" does not fall within the range of the standard value±the standard deviation preliminarily calculated for an analyte protein.

In addition, in the method for predicting a prognosis of the present invention, the expression level of an analyte protein may be determined via immunohistochemical staining with the use of tissue collected from a target patient. In such case, the percentage of the number of cells in which the expression of an analyte protein has been confirmed is calculated as a result of determination of the expression level, such cells having been obtained from the entirety of the tissue subjected to immunohistochemical staining. Then, if the percentage of myosin IIA-positive cells is 50% or greater, it can be predicted that the patient has a poor prognosis. Also, if the proportion of vimentin-positive cells is 25% or greater, it can be predicted that the patient has a poor prognosis.

With the use of a method and a test kit for predicting/determining a prognosis of the present invention, the postoperative prognosis of a lung adenocarcinoma patient can be preliminarily predicted with significantly excellent sensitivity and/or excellent specificity. The term "sensitivity" used herein refers to the positive rate in a group with a poor prognosis. The term "specificity" used herein refers to the negative rate in a group with a good prognosis.

According to the present invention, it becomes possible to administer an anti-cancer agent in a selective manner to a patient who can be predicted to have a poor prognosis by preliminarily predicting the prognosis. In addition, no recurrence was observed among lung adenocarcinoma patients with myosin IIA- and vimentin-negative results obtained by the immunohistochemical staining method, regardless of whether or not postoperative UFT administration took place. Therefore, it can be predicted that such patients belong to a patient group that can avoid postoperative UFT administration. Even in a case in which an anti-cancer agent presents no problems in terms of safety, it is highly effective to avoid unnecessary administration of such agent in terms of medical economy.

The present invention is hereafter described in greater detail with reference to the following examples, although the technical scope of the present invention is not limited thereto. In the Examples, the method disclosed in Patent Document 1 was applied to clinical specimens obtained in practice. Then, a group of proteins that allow prediction of the prognosis of an early lung adenocarcinoma patient treated with postoperative adjuvant chemotherapy was searched for and identified. Accordingly, it was verified that such proteins can be used as diagnosis markers.

Example 1

Surgically excised tissue specimens of early lung adenocarcinoma patients who had been diagnosed as stage I by pathological tissue diagnosis were subjected to protein extraction/digestion by a method described below, followed by determination with an LC-MS instrument. At a later date, the obtained profiles were classified into the following groups: a group with metastatic recurrence after the implementation of postoperative adjuvant chemotherapy; a group with nonmetastatic recurrence after the implementation of postoperative adjuvant chemotherapy; a group with metastatic recurrence after the non-implementation of postoperative adjuvant chemotherapy; and a group with nonmetastatic recurrence after the non-implementation of postoperative adjuvant chemotherapy. Signals significantly varying among the groups were picked up and subjected to MS/MS analysis for protein identification.

Samples

Samples used for LC-MS/MS determination/analysis were surgically excised early lung adenocarcinoma tissue specimens obtained from 24 cases from 1995 to 2001. These samples had been diagnosed as stage I by pathological tissue diagnosis and preserved immediately after surgical resection at −80° C. Among 24 early lung adenocarcinoma cases, 11 cases were treated with a postoperative adjuvant chemotherapy with UFT (tegafur+uracil) in the postoperative period, 5 cases were found to exhibit metastatic recurrence within the 2-year postoperative period corresponding to "metastatic recurrence after the implementation of postoperative adjuvant chemotherapy (U1R1)," and 6 cases were found to exhibit nonmetastatic recurrence within the 5-year postoperative period corresponding to "nonmetastatic recurrence after the implementation of postoperative adjuvant chemotherapy (U1R0)." Further, among 24 early lung adenocarcinoma cases, follow-up was carried out for 13 cases without any adjuvant chemotherapy with UFT or a different agent in the postoperative period. Of these, 6 cases were found to exhibit metastatic recurrence within the 2-year postoperative period corresponding to "metastatic recurrence after the non-implementation of postoperative adjuvant chemotherapy (U0R1)" and 7 cases were found to exhibit nonmetastatic recurrence within the 5-year postoperative period corresponding to "nonmetastatic recurrence after the non-implementation of postoperative adjuvant chemotherapy (U0R0)."

Preparation of Samples

Samples used for LC-MS/MS determination/analysis were obtained by disrupting cryopreserved tissue sections (analytes) in a phosphate-buffered saline (PBS) solution at 4° C. In order to inhibit non-specific degradation caused by proteases, a mixture containing protease activity inhibitors (a protease inhibitor cocktail tablet; produced by Roche Diagnostics) had been preliminarily dissolved in the PBS solution. After shaking agitation of the suspension obtained by disruption for 10 minutes, the suspension was centrifuged (conditions: 52000×g, 4° C., 20 minutes). (The supernatant obtained by this operation is hereinafter referred to as a soluble fraction.) The obtained soluble fraction was preserved at −80° C. Meanwhile, the precipitate was repeatedly suspended three times in the PBS solution and centrifuged under the above conditions. Thereafter, the resultant was dissolved in a solution containing sodium dodecylsulfate (SDS). The composition of the resulting solution comprised PBS (containing a protease activity inhibitor mixture) and 5% w/v SDS. (This solution is hereinafter referred to as an insoluble fraction.)

Determination of Total Protein Concentration

The protein concentrations of both fractions were determined by a modified Lowry method. Bovine serum albumin was used as a standard protein for creation of a standard curve.

SDS-Polyacrylamide Gel Electrophoresis (PAGE)

A portion of each soluble and insoluble fraction in a volume corresponding to approximately 75 μg of total protein was obtained. Each portion was mixed with an egg-white lysozyme aqueous solution (150 pmol). Then, each liquid mixture was dried under vacuum. Each dried sample was dissolved in an SDS-PAGE sample buffer (62.5 mM Tris-hydrochloric acid (pH 6.8), 2% w/v SDS, 5% v/v 2-mercaptoethanol, 10% v/v glycerol, and 0.0025% w/v bromophenol blue) (70 μL). Each dissolved solution was shaken at 37° C. for 60 minutes. A portion (50 μL) of each resultant was subjected to SDS-PAGE established by Laemmli. The polyacrylamide gel used for SDS-PAGE was a discontinuous buffer system, which was specifically composed of a concentration gel (pH 6.8) constituting the upper portion and a separation gel (pH 8.8) constituting the lower portion. The polyacrylamide gel concentrations were 4% and 12.5%, respectively. The gel sample size was 14 cm in width, 14 cm in height, and 1 mm in thickness. The current for electrophoresis was kept at a constant level of 20 mA. Electrophoresis was terminated when the electrophoretic front of the bromophenol blue dye reached a point approximately 2 mm inside the separation gel from the boundary surface between the concentration gel and the separation gel. For each sample, a section extending from the boundary surface between the concentration gel and the separation gel to the electrophoretic front was excised. The gel section size was approximately 4×10×1 mm.

Trypsin Digestion in Gel

The above sections were immersed in an aqueous solution containing 40% methanol and 10% acetic acid (approximately 1 mL), followed by shaking. Thus, protein contained in gel was fixed. The gel sections were cut into cubes each with a side of approximately 1 mm, followed by treatment of the protein in gel according to procedures described below. In order to modify sulfhydryl (SH) groups in cysteine residues, a reduction reaction with dithiothreitol and then an alkylation reaction with iodoacetamide were carried out. Subsequently, gel pieces were washed with a sufficient amount of water and dehydrated with acetonitrile. Water remaining in gel pieces and acetonitrile were dried under vacuum. A trypsin solution was added to the gel pieces, followed by incubating at 37° C. for 16 hours for a digestion reaction. Peptide fragments contained in the gel pieces were subjected to a single instance of extraction with an aqueous solution containing 25 mM ammonium bicarbonate/50% acetonitrile, followed by two-times of extraction with an aqueous solution containing 5% formic acid/50% acetonitrile. The extracted solutions were mixed together into a single container, followed by concentration under vacuum.

LC-MS/MS

In order to obtain a three-dimensional profile of each peptide sample, each peptide sample was analyzed by operations with the use of an instrument described below (Proteomics 5 (2005)856-864). First, each peptide sample was separately dissolved in an aqueous solution containing 0.1% trifluoroacetic acid (100 μL). The resulting solutions were designated as analytes.

A portion of each analyte (10 μl) was desalted and concentrated with the use of a Peptide CapTrap cartridge (inner diameter: 0.5 mm; length: 2 mm; produced by Michrom BioResources) and introduced into a MAGIC MS™ $C_{18}$ capillary column (inner diameter: 0.2 mm; length: 50 mm; particle size: 3 μm; and pore size: 200 Å). Elution of each peptide was carried out with the use of a Paradigm MS-4™ HPLC system (Michrom BioResources). In the above case, the HPLC mobile phase A was designated as a solvent obtained by mixing formic acid, acetonitrile, and water at a volume ratio of 0.1:2:98, provided that the mobile phase B mixing ratio was 0.1:90:10. In addition, an increase in the mobile phase B concentration was predetermined in the form of a linear gradient of 5% to 95%, for continuous elution of peptide fragments. The flow rate was set to approximately 1 μL/min.

The LC eluent was directly interfaced into an ion source of a Finnigan LTQ™ ion trap mass spectrometer (ThermoElectron) via a Frotis™ Tip ESI emitter (inner diameter: 20 μm) (produced by AMR). The position of an ESI emitter can be finely adjusted in terms of the distance from a heated capillary. The spray voltage was directly applied to an eluent but not to a needle. For analysis noise reduction, a nitrogen gas was introduced into an ion source at a flow rate of 2 arb and the spray voltage was set to 2.0 kV.

Data Analysis

Data analysis was carried out with the use of the i-OPAL program described in Patent Document 1 for each case. Specific procedures are described below.

Analysis Procedures

All full MS data were analyzed using the i-OPAL semi-quantitative LC-MS data analysis system (i-OPAL algorithm). First, the signal intensity of the full MS scan was normalized so as to adjust the total signal intensity for each sample to an identical level. Ion signals derived from egg-white lysozyme that had been injected as an internal standard substance or from an endogenous protein common to the samples were selected as i-OPAL alignment markers. The i-OPAL alignment program was used for alignment of non-linearly fluctuating LC elution time axes for LC-MS data and eventually for superposition of the data for the soluble fraction and the data for the insoluble fraction for obtaining common LC-MS data. Analysis of variance (ANOVA) was used to select marker candidate signals, which had been found to obviously have different intensities in a specific case group, from the LC-MS data eventually superposed above. For ANOVA, a Spotfire DecisionSite package was used.

Database Search

All MS/MS data were subjected to a search within the Swiss-Prot human subset database and the RefSeq protein sequence database with the use of a Mascot search engine (Matrix Science, London, UK. [http://www.matrixscience.com]). A database search was carried out under the following conditions: Fixed modification of cysteine residues (carbamidomethylation, +57Da); variable modification of methionine residues (oxidation, +16Da); peptide mass error tolerance of ±2.0 Da; and fragment m/z error tolerance of ±0.8 Da.

Results

After alignment with the use of i-OPAL, 13,136 peaks and 14,984 peaks were detected for the soluble fraction and the insoluble fraction, respectively. With the use of Spotfire, candidate signals were narrowed down under the following conditions:

(1) the score for search results obtained with the use of the Mascot search engine was 50 or more; and
(2) P values obtained by ANOVA were $1\times10^{-5}$ or less and $1\times10^{-6}$ or less for the soluble fraction and the insoluble fraction, respectively.

Figure 1A:
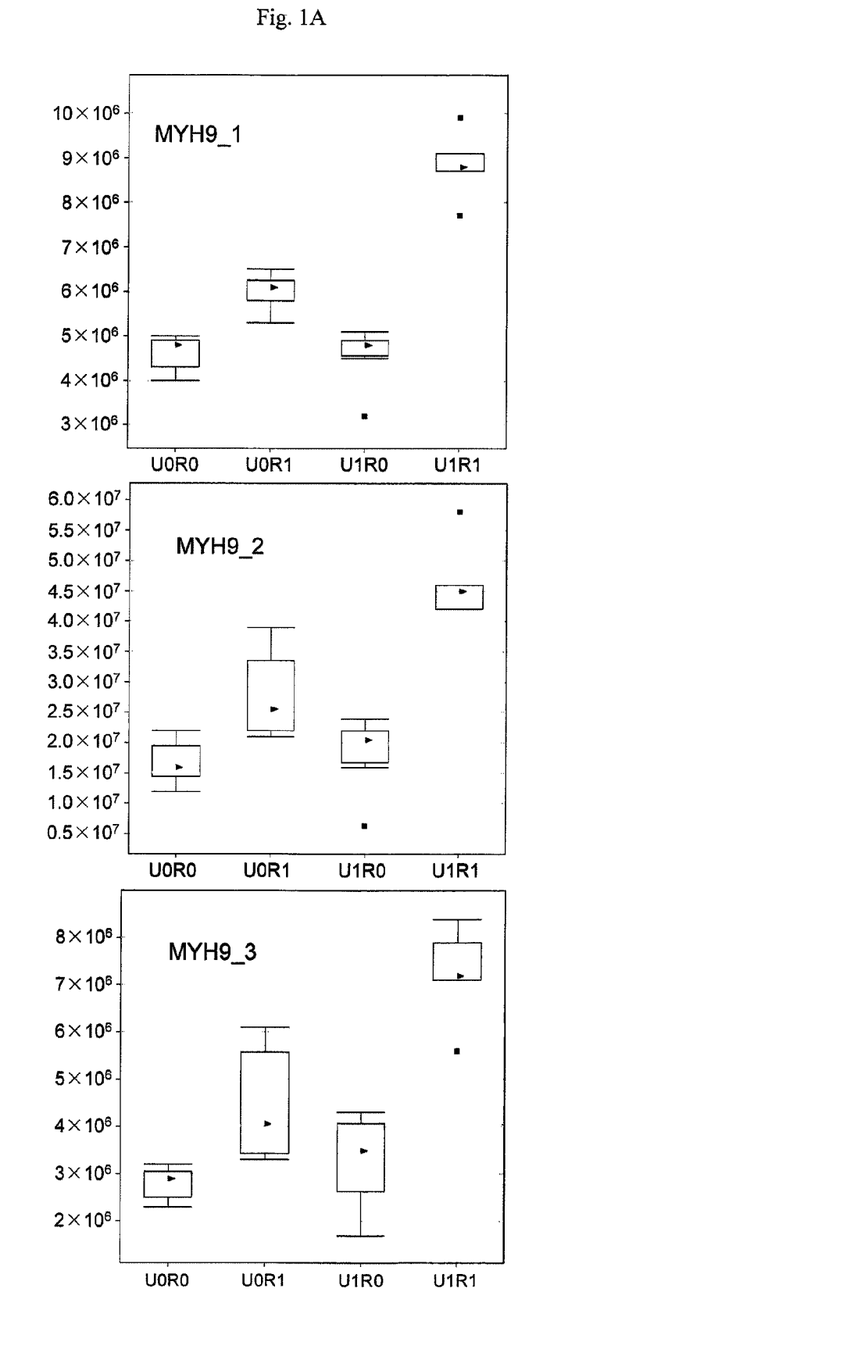
Figure 1B:
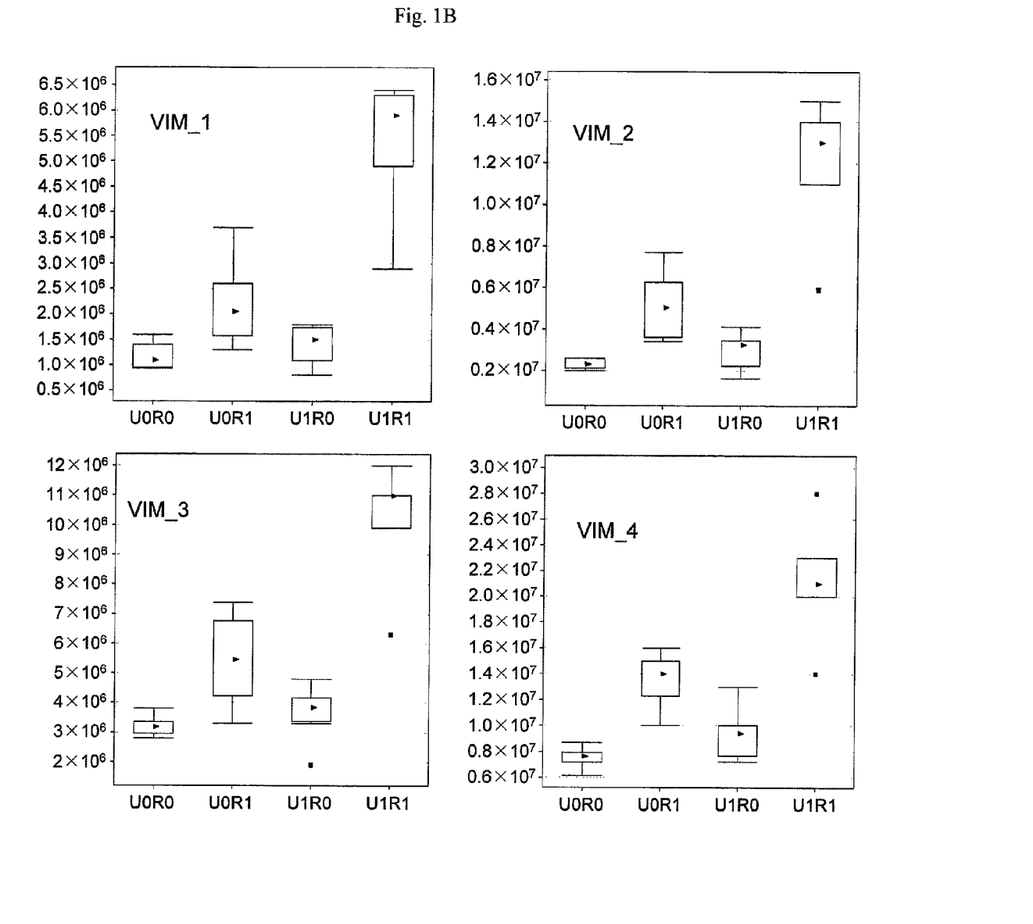

Under the above conditions, candidate peaks were narrowed down to 23 peaks and 28 peaks for the soluble fraction and the insoluble fraction, respectively. Further, a plurality of different amino acid sequences were detected from the plurality of candidate peaks. Myosin IIA and vimentin showing similar signal intensity patterns were selected as final biomarker candidates. Table 2 above lists the peptide sequences thereof. In addition, FIGS. 1A and 1B show results obtained by comparing peptide signal intensities via LC-MS analysis in this Example. FIG. 1A shows a distribution of signal intensities of a plurality of peptide ions generated from myosin IIA. Three peptide signal patterns shown in FIG. 1A were found to belong to myosin IIA via MS/MS. There was a significant difference between the U1R1 group and the other groups ($P<9.7\times10^{-7}$). In addition, FIG. 1B shows a distribution of signal intensities of a plurality of peptide ions generated from vimentin. Four peptide signal patterns shown in FIG. 1B were found to belong to vimentin via MS/MS. There was a significant difference between the U1R1 group and the other groups ($P<3.8\times10^{-7}$).

Regarding all signal patterns, the pattern of signal intensities for the patient group with metastatic recurrence after the implementation of postoperative adjuvant chemotherapy (U1R1) were obviously different (very high) from those for the other patient groups.

Example 2

Proteins identified as prognosis factors in the above Example were verified by a method described below with the use of surgically excised tissue samples from early lung adenocarcinoma patients diagnosed as stage I by pathological tissue diagnosis (which were cases totally different from the cases used in Example 1).

Samples

Samples used for verification of prognosis factor proteins of early lung adenocarcinoma identified in Example 1 were formalin-fixed paraffin-embedded specimens of surgically excised early lung adenocarcinoma tissue samples obtained from 90 cases from 1995 to 2001. All cases were treated by radical surgery for lung cancer and diagnosed as being stage I by postoperative pathological tissue diagnosis. The samples were evaluated in terms of the recurrence or nonrecurrence with postoperative chest X-ray photographs and serum tumor marker levels (CEA, CA19-9, and SLX) that had been taken every 3 months and head and thoracoabdominal computed tomography (CT) and bone scintigraphy images that had been taken every 6 months during the postoperative period. When it was difficult to identify the recurrence or nonrecurrence based on the results of the above tests, a definitive diagnosis was given based on cytochemical or pathological tests. 51 cases out of 90 cases with stage-I lung adenocarcinoma were treated with postoperative adjuvant chemotherapy with UFT in the postoperative period. Among them, 24 cases with "metastatic recurrence after the implementation of postoperative adjuvant chemotherapy" were found to exhibit metastatic recurrence within the 2-year postoperative period and 27 cases with "nonmetastatic recurrence after the implementation of postoperative adjuvant chemotherapy" did not exhibit metastatic recurrence within the 5-year postoperative period. Further, among 90 cases of early lung adenocarcinoma, follow-up was carried out for 39 cases without any postoperative adjuvant chemotherapy with UFT or a different agent. Among them, 17 cases with "metastatic recurrence after the non-implementation of postoperative adjuvant chemotherapy" were found to exhibit postoperative metastatic recurrence and 22 cases with "nonmetastatic recurrence after the non-implementation of postoperative adjuvant chemotherapy did not exhibit postoperative metastatic recurrence.

Immunohistochemical Staining

Formalin-fixed paraffin-embedded specimens obtained from early lung adenocarcinoma cases were each sliced to a thickness of 4 μm and placed on glass slides. The tissue specimens were subjected to deparaffinization with methanol and xylene, followed by 0.01% trypsin treatment and autoclave treatment at 100° C. for 10 minutes. Further, the specimens were subjected to 0.5% methanol/100% hydrogen peroxide treatment, followed by deactivation of endogenous peroxidase with 2% normal serum/PBS. Then, each specimen was reacted overnight at 4° C. with an anti-myosin IIA mouse monoclonal antibody (produced by abcam, clone ab24762) and an anti-vimentin mouse monoclonal antibody (produced by Dako Cytomation). Thereafter, each specimen was reacted with an anti-mouse IgG antibody and an avidin-biotin complex antibody, followed by a DAB reaction with 0.06% 3,3'-diaminobenzidine tetrahydrochloride in a Tris-buffered saline solution containing 0.03% hydrogen peroxide under a microscope. Nuclear staining was carried out with the use of Meyer's hematoxylin.

Determination of Immunohistochemical Staining Results

Regarding the expression of myosin IIA and vimentin in cancer cells, a cancer sample was compared with a normal bronchial epithelial sample obtained from a same-type specimen of a same-type case that was used as an internal control. The degree of cytoplasm staining in cancer cells was determined.

Statistical Analysis of Immunohistochemical Staining Results

For statistical analysis of immunohistochemical staining results, SPSS ver. 15 (clinical statistics software; SPSS Inc.) was used. The survival period with nonrecurrence was determined by the Kaplan-Meier method. The survival rate for each patient group was determined by a log-rank test. Statistical significance was determined with a p-value of <0.05.

Results

Figure 2:
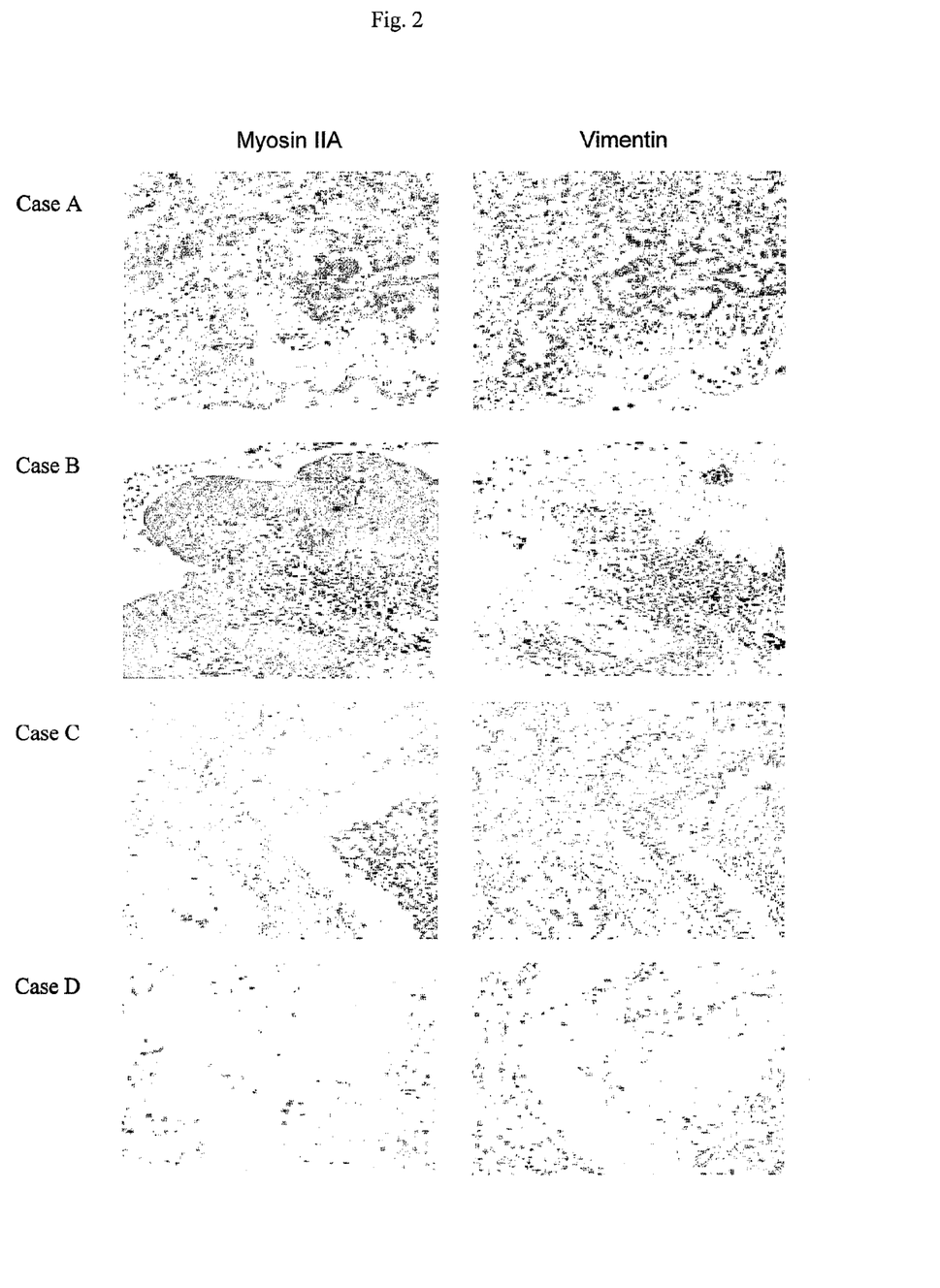
FIG. 2 shows typical immunohistochemical staining results obtained with the use of an anti-myosin IIA antibody and an anti-vimentin antibody. Case A shows photographs of myosin IIA- and vimentin-positive immunohistochemical staining results. Case B shows photographs of myosin IIA-positive and vimentin-negative immunohistochemical staining results. Case C shows photographs of myosin IIA-negative and vimentin-positive immunohistochemical staining results. Case D shows photographs of myosin IIA- and vimentin-negative immunohistochemical staining results.

FIG. 2 shows typical immunohistochemical staining results for myosin IIA and vimentin, which are proteins that were verified to be significantly expressed in early lung adenocarcinoma cases with poor prognosis. In addition, Table 3 lists staining results for the individual proteins.

TABLE 3

|  |  | No. of Patients (%) |
|---|---|---|
| Myosin | Positive | 75 (83.3%) |
|  | Negative | 15 (16.7%) |
| Vimentin | Positive | 48 (53.3%) |
|  | Negative | 42 (46.7%) |
| Both (myosin and vimentin) positive |  | 42 (46.7%) |
| Both (myosin and vimentin) negative |  | 9 (10.0%) |

Myosin IIA and vimentin were expressed in the cytoplasm. Regarding myosin IIA, when expression was observed in 50% or more of cells, the result was determined as positive. Regarding vimentin, when expression was observed in 25% or more of cells, the result was determined as positive. Among 90 cases, 75 cases (83.3%) were found to be myosin IIA-positive and 15 cases (16.7%) were found to be myosin IIA-negative. In addition, 48 cases (53.3%) were found to be vimentin-positive and 42 cases (4.7%) were found to be vimentin-negative. In addition, 42 cases (46.7%) were myosin IIA- and vimentin-positive and 9 cases (10%) were myosin IIA- and vimentin-negative. No relevance was confirmed between the immunohistochemical reactivity of myosin IIA and that of vimentin.

Figure 3:
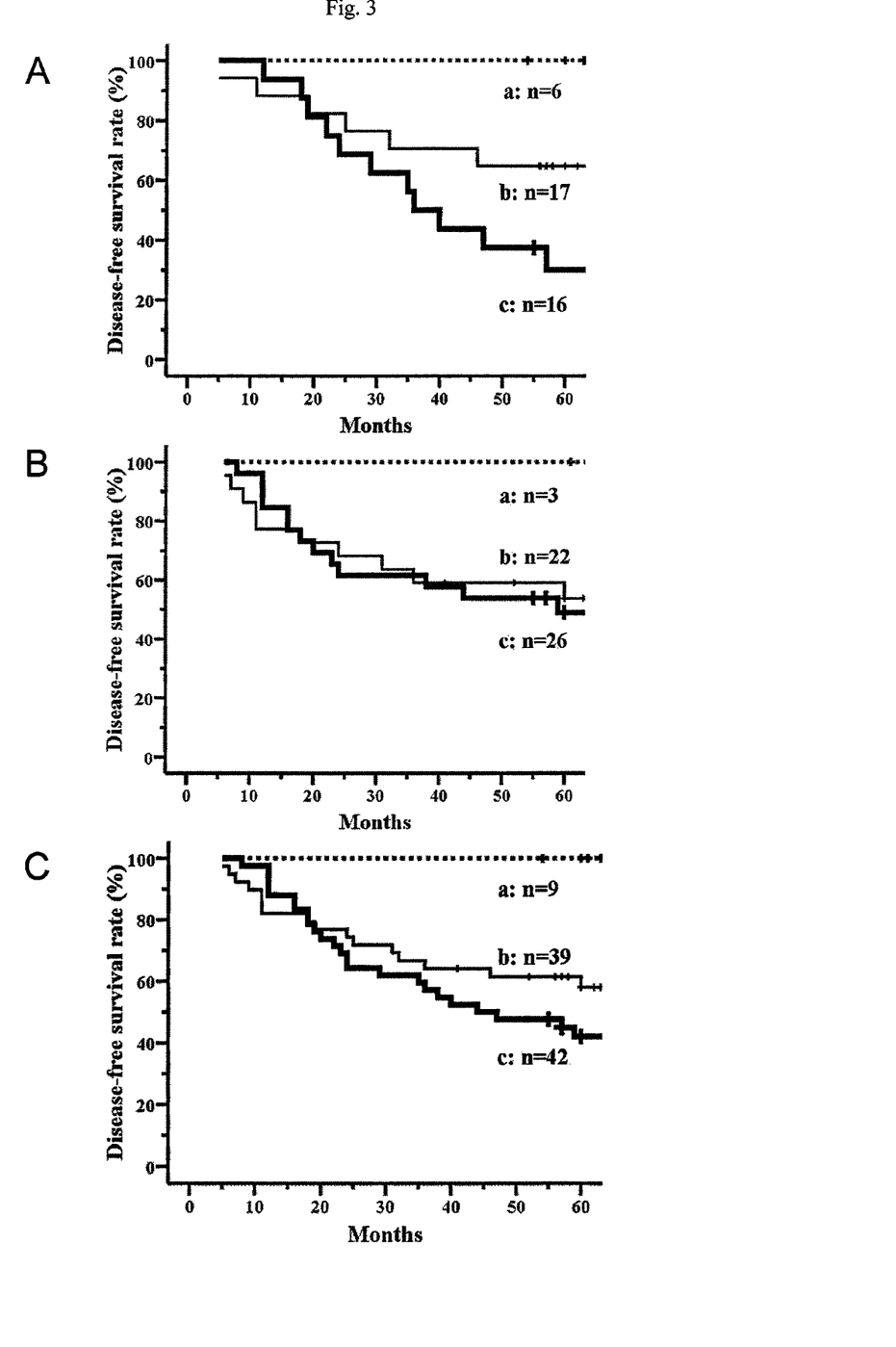
FIGS. 3A and 3B show survival curves based on myosin IIA and vimentin immunohistochemical staining results for the cases followed up without postoperative adjuvant chemotherapy with UFT (A) and the cases treated with postoperative adjuvant chemotherapy with UFT (B).
FIG. 3C shows nonrecurrence survival curves for all cases subjected to immunohistochemical staining (C).

FIGS. 3A and 3B show survival curves of immunohistochemical staining results for cases followed up without postoperative adjuvant chemotherapy with UFT (A) and cases treated with postoperative adjuvant chemotherapy with UFT (B). In FIGS. 3A, 3B, and 3C, line "a" represents myosin IIA- and vimentin-negative cases, line "b" represents myosin IIA-negative and vimentin-positive cases or myosin IIA-positive and vimentin-negative cases, and line "c" represents myosin IIA- and vimentin-positive cases.

Regardless of whether or not postoperative adjuvant chemotherapy was implemented, the 5-year survival rate was 100% for the patients corresponding to both-negative cases. Among the patients followed up without postoperative adjuvant chemotherapy, there was a statistically significant difference between the cases with negative results of the expression of myosin IIA and vimentin (group "a") and the cases with positive results of the expression of myosin IIA and vimentin (group "c") (p=0.011) (FIG. 3A). There was no statistically significant difference among the patients treated with postoperative adjuvant chemotherapy (FIG. 3B). In the cases with positive results of the expression of myosin IIA and vimentin (group "c"), an increase by approximately 19% of the 5-year survival rate was confirmed for the patients treated with postoperative adjuvant chemotherapy with UFT. However, there was no statistically significant difference between the patients treated with postoperative adjuvant chemotherapy and the patients followed up without postoperative adjuvant chemotherapy.

There was a statistically significant difference between the cases with negative results of the expression of myosin IIA and vimentin (group "a") and the cases with positive results of the expression of myosin IIA and vimentin (group "c") based on non-recurrence survival curves for all cases (P=0.006) (FIG. 3C). There was a statistically significant difference between the cases with positive results of either the expression of myosin IIA or the expression of vimentin (group "b") and the cases with negative results of the expression of both myosin IIA and vimentin (group "c") (P=0.029) (FIG. 3C).

Regardless of whether or not postoperative adjuvant chemotherapy was implemented, a good prognosis was obtained for the patients with negative results of the expression of both myosin IIA and vimentin (the 5-year survival rate: 100%). Therefore, it has been verified that the above two proteins serve as factors for predicting the prognosis of a patient and as biomakers that are very useful for selection of a patient who does not need to receive postoperative adjuvant chemotherapy. Further, an increase by approximately 19% of the 5-year survival rate was confirmed for the patients treated with postoperative adjuvant chemotherapy with UFT among the cases with positive results of the expression of myosin IIA and vimentin, although no statistically significant difference was confirmed. Accordingly, it has been confirmed that there is a patient group that can be improved in terms of prognosis by postoperative adjuvant chemotherapy, among patient groups originally having a poor prognosis.

Industrial Applicability

According to the present invention, a method and a test kit for predicting postoperative prognosis, whereby the postoperative prognosis of a lung adenocarcinoma patient can be preliminarily predicted or a diagnosis can be given with excellent reliability during treatment, can be provided.

All publications, patents, and patent applications cited herein are incorporated herein by reference in their entirety.

The invention claimed is:

1. A method for predicting a postoperative prognosis of a lung adenocarcinoma patient, comprising:
   step (a) of determining expression levels of myosin IIA and/or vimentin in a biological sample collected from a lung adenocarcinoma patient; and
   step (b) of predicting or determining a prognosis of the lung adenocarcinoma patient based on the expression levels of myosin IIA and/or vimentin obtained as a result of determination.

2. The method for predicting a prognosis of a lung adenocarcinoma patient according to claim 1, wherein the expression level of at least one peptide selected from the group of peptides having the SEQ ID Nos: listed in the PEPTIDE_SEQ column of Table 1 is determined in step (a)

TABLE 1

| Protein Name | Name | Peptide | Fraction | PEPTIDE_SEQ |
|---|---|---|---|---|
| Myosin IIA | MYH9 | MYH9_1 | Insoluble | SEQ ID No: 1 |
|  |  | MYH9_2 | Insoluble | SEQ ID No: 2 |
|  |  | MYH3_3 | Insoluble | SEQ ID No: 3 |
| Vimentin | VIM | VIM_1 | Insoluble | SEQ ID No: 4 |
|  |  | VIM_2 | Insoluble | SEQ ID No: 5 |

TABLE 1-continued

| Protein Name | Name | Peptide | Fraction | PEPTIDE_SEQ |
|---|---|---|---|---|
|  |  | VIM_3 | Insoluble | SEQ ID No: 6 |
|  |  | VIM_4 | Insoluble | SEQ ID No: 7. |

3. The method for predicting a prognosis of a lung adenocarcinoma patient according to claim 1, wherein the expression levels of myosin IIA and/or vimentin are determined by immunohistochemical staining with the use of a monoclonal antibody in step (a).

4. The method for predicting a prognosis of a lung adenocarcinoma patient according to claim 1, wherein the expression levels of myosin IIA and/or vimentin are determined by allowing an extract obtained from the biological sample collected from the lung adenocarcinoma patient to come into contact with a support on which a monoclonal antibody has been immobilized in step (a).

5. The method for predicting a prognosis of a lung adenocarcinoma patient according to any one of claims 1-4, wherein the lung adenocarcinoma patient is an early lung adenocarcinoma patient diagnosed as stage I by pathological tissue diagnosis.

6. The method for predicting a postoperative prognosis of a lung adenocarcinoma patient according to any one of claims 1-4, wherein step (b) further comprises obtaining positive or negative results from a lung adenocarcinoma patient following postoperative adjuvant chemotherapy;

wherein positive results are obtained when expression levels of myosin IIA is observed in 50% or more of cells and/or expression levels of vimentin is observed in 25% or more of cells; and wherein positive results are indicative of a low survival rate and negative results are indicative of a high survival rate.

* * * * *

```
SEQUENCE LISTING

<160> NUMBER OF SEQ ID NOS: 7

<210> SEQ ID NO 1
<211> LENGTH: 19
<212> TYPE: PRT
<213> ORGANISM: Homo sapiens

<400> SEQUENCE: 1

Ile Arg Glu Leu Glu Ser Gln Ile Ser Glu Leu Gln Glu Asp Leu Glu
1               5                   10                  15

Ser Glu Arg

<210> SEQ ID NO 2
<211> LENGTH: 17
<212> TYPE: PRT
<213> ORGANISM: Homo sapiens

<400> SEQUENCE: 2

Lys Ala Asn Leu Gln Ile Asp Gln Ile Asn Thr Asp Leu Asn Leu Glu
1               5                   10                  15

Arg

<210> SEQ ID NO 3
<211> LENGTH: 16
<212> TYPE: PRT
<213> ORGANISM: Homo sapiens

<400> SEQUENCE: 3

His Glu Met Pro Pro His Ile Tyr Ala Ile Thr Asp Thr Ala Tyr Arg
```

```
                1               5                    10                    15

<210> SEQ ID NO 4
<211> LENGTH: 15
<212> TYPE: PRT
<213> ORGANISM: Homo sapiens

<400> SEQUENCE: 4

Glu Thr Asn Leu Asp Ser Leu Pro Leu Val Asp Thr His Ser Lys
1               5                   10                  15

<210> SEQ ID NO 5
<211> LENGTH: 10
<212> TYPE: PRT
<213> ORGANISM: Homo sapiens

<400> SEQUENCE: 5

Asn Leu Gln Glu Ala Glu Glu Trp Tyr Lys
1               5                   10

<210> SEQ ID NO 6
<211> LENGTH: 10
<212> TYPE: PRT
<213> ORGANISM: Homo sapiens

<400> SEQUENCE: 6

Leu Gly Asp Leu Tyr Glu Glu Glu Met Arg
1               5                   10

<210> SEQ ID NO 7
<211> LENGTH: 19
<212> TYPE: PRT
<213> ORGANISM: Homo sapiens

<400> SEQUENCE: 7

Leu Leu Gln Asp Ser Val Asp Phe Ser Leu Ala Asp Ala Ile Asn Thr
1               5                   10                  15

Glu Phe Lys
```